Figure 1:
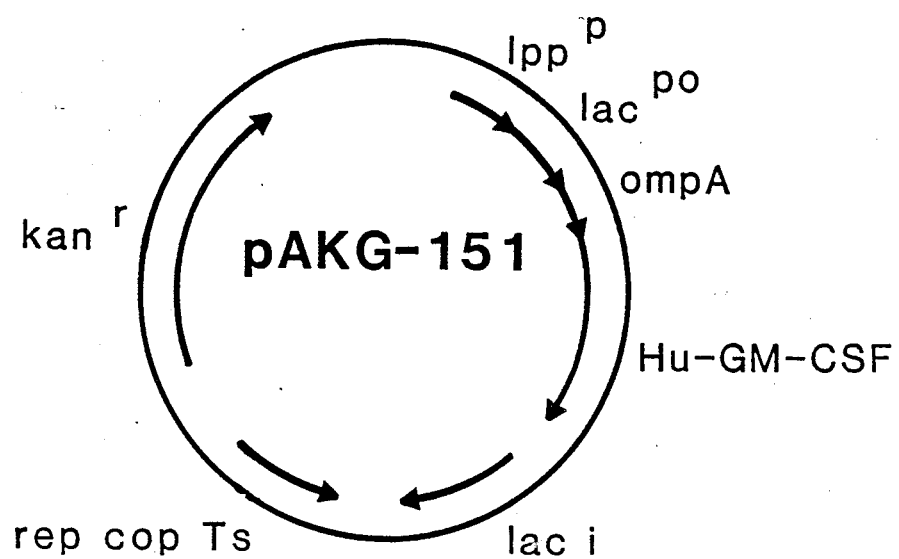

United States Patent [19]

Leibowitz et al.

[11] Patent Number: 4,912,200
[45] Date of Patent: Mar. 27, 1990

[54] EXTRACTION OF GRANULOCYTE MACROPHAGE COLONY STIMULATING FACTOR FROM BACTERIA

[75] Inventors: Paul Leibowitz, Hackensack; Yair Alroy, Parsippany, both of N.J.

[73] Assignee: Schering Corporation, Kenilworth, N.J.

[21] Appl. No.: 48,187

[22] Filed: May 11, 1987

[51] Int. Cl.$^4$ .............................................. C07K 3/12
[52] U.S. Cl. .................................... 530/351; 530/395; 530/412; 530/418; 530/419; 530/422; 530/427; 530/825; 435/69.5
[58] Field of Search ............... 530/412, 351, 395, 418, 530/419, 422, 427, 825; 435/68

[56] References Cited

U.S. PATENT DOCUMENTS

| | | | |
|---|---|---|---|
| 4,364,863 | 12/1986 | Leibowitz et al. | 424/85.7 |
| 4,675,387 | 6/1987 | Kerant | 530/412 |
| 4,801,686 | 1/1989 | Kronheim | 530/412 |

FOREIGN PATENT DOCUMENTS

| | | |
|---|---|---|
| 3329624 | 3/1984 | Fed. Rep. of Germany . |
| 3432196 | 3/1986 | Fed. Rep. of Germany . |

OTHER PUBLICATIONS

De Lamarter et al., *EMBo*, 4(10), 1985, pp. 2575-2581.
Clark et al., *Science* 236, 1987, pp. 1229-1237.
Cantrell et al., *PNAS* 82, 1985, pp. 6250-6254.

*Primary Examiner*—Garnette D. Draper
*Attorney, Agent, or Firm*—Norman C. Dulak; James R. Nelson; Stephen I. Miller

[57] ABSTRACT

A method of extracting granulocyte macrophage colony stimulating factor (GM-CSF) from GM-CSF-expressing bacterial cells comprising treating a suspension of GM-CSF-containing bacterial cells with an acid and an enhancing agent, removing substantially all of the suspension liquid from the cells, preparing a second suspension of the acidified cells, neutralizing said second suspension, and separating the GM-CSF containing liquid from the suspended cells.

18 Claims, 1 Drawing Sheet

EXTRACTION OF GRANULOCYTE MACROPHAGE COLONY STIMULATING FACTOR FROM BACTERIA

BACKGROUND OF THE INVENTION

The present invention relates to extraction of granulocyte/macrophage colony stimulating factor (GM-CSF) from GM-CSF-expressing bacteria.

Granulocyte macrophage colony stimulating factor is believed to be a potential therapeutic agent against infection and cancer. Clinical testing and widespread use of GM-CSF have been delayed due to the unavailability of sufficient quantities of the material and the great expense of obtaining GM-CSF from natural sources. Recombinant DNA techniques have been used to create bacteria capable of expressing GM-CSF. See, for example, DeLamarter, et al., EMBO J., Vol. 4, 2575–2581 (1985). Fermentation of such bacteria is expected to yield sufficient quantities of GM-CSF at substantially lower cost than would be possible utilizing natural sources of GM-CSF. However, clinical use of GM-CSF also requires high purity material that is not contaminated by cell constituents or cell debris of the GM-CSF-expressing bacteria. Contamination by such impurities could result in adverse reactions or in test results that are not reproducible. Accordingly, extraction of GM-CSF from the cells of GM-CSF-expressing bacteria is sufficiently high purity and yield for clinical use has been a major problem.

SUMMARY OF THE INVENTION

The present invention is based on the discovery that GM-CSF can be extracted from GM-CSF-expressing bacteria in high yield and purity by treating a suspension of GM-CSF-containing bacterial cells with an acid and an enhancing agent, removing and discarding substantially all of the suspension liquid from the cells, preparing a second suspension of the treated cells, neutralizing said second suspension and separating the GM-CSF-containing liquid from the suspended cells. In accordance with the method of the present invention, GM-CSF is obtained from the cells without the need for mechanical or enzymatic disruption of the cell surface. The method of this invention allows recovery of GM-CSF in a manner which significantly reduces contamination by cell constituents and provides subsequent purification easier and less expensive.

BRIEF DESCRIPTION OF THE DRAWING

FIG. 1 is a construction map of plasmid pAKG-151.

DETAILED DESCRIPTION

The present invention provides a method for extracting GM-CSF from GM-CSF-expressing bacterial cells comprising:

(a) treating a suspension of GM-CSF containing bacterial cells with an acid and an enhancing agent;
(b) removing substantially all of the suspension liquid from the treated cells;
(c) preparing a second suspension of the treated cells;
(d) neutralizing said second suspension; and
(e) separating the GM-CSF containing liquid from the suspended treated cells.

In carrying out the method of the present invention, acid is added to a suspension of GM-CSF-expressing cells to adjust the pH to about 1.5 to 3.0, and preferably to a pH of about 2.0 to 2.2. Examples of suitable acids that can be utilized in this invention are hydrochloric acid, nitric acid, phosphoric acid and sulfuric acid. Phosporic acid is the preferred acid.

In order to achieve complete cell deactivation and/or to improve the yield of extracted GM-CSF, it has been discovered that certain reagents, hereinafter referred to as "enhancing agents" must be added to the suspension of GM-CSF-expressing cells along with the acid. Examples of suitable enhancing agents include chaotropic ions, such as trichloroacetate, perchlorate, thiocyanate and guanidine; non-chaotropic salts, such as sodium chloride, sodium phosphate; and non-ionic chaotropes such as urea. Chaotropic ions are the preferred enhancing agents. Trichloroacetic acid is the most preferred enhancing agent (about 0.1M to 2.0M depending on such variables as cell density, pH and salt composition).

When the enhancing agent is a chaotropic ion it may be added either as a chaotropic salt, such as sodium thiocyanate or guanidine chloride, or as a chaotropic acid, such as trichloroacetic acid or perchloric acid. If a chaotropic acid is used, then it may partially or completely replace the primary acid.

In one embodiment of the acidification step of the method of this invention, phosphoric acid is added to the suspension to lower the pH to about 4 to 5, preferably 4.5 and then trichloroacetic acid is added to lower the pH to 2.0.

If the temperature is too low then the bacteria will not be killed fast enough during the acid treatment. If the temperature is too high then GM-CSF may be altered. The temperature range for the acid treatment should be from about 10° C. to about 40° C., and preferably 25° C.

After treating the cell suspension with acid and an enhancing agent, all subsequent steps of the method of this invention are carried out at a temperature of from about 0° C. to about 40° C., preferably 0°–4° C.

After the cell suspension is treated with an acid and an enhancing agent, the cells are separated from the treatment liquid by microfiltration, centrifugation or the like, preferably by centrifugation, and resuspended in an aqueous buffer solution or in water. Examples of buffers that may be used in resuspending the pellet are sodium phosphate, potassium phosphate and tris (Hydroxymethyl) aminomethane hydrochloride. The preferred buffer is sodium phosphate.

The cell suspension is neutralized to a pH of about 6.0 to 9.0, preferably 7.2–7.6. Examples of suitable bases that may be used in the neutralization step are sodium hydroxide, potassium hydroxide and the like.

Examples of bacteria that can be altered by recombinant DNA techniques to produce GM-CSF and from which GM-CSF may then be extracted using the method of the present invention are *E. coli, Bacillus subtilis, Streptomyces coelicolor,* and the like. The preferred bacterium is *E. coli.*

The method of the present invention may be used with bacteria that express different forms of GM-CSF, for example, human GM-CSF, see Lee et al., Proc. Natl. Acad. Sci. USA, Vol. 82, 4060–4064 (1985), and murine GM-CSF, see Burgess et al., J. Biol. Chem., Vol. 252, 1998–2033 (1977).

The following example describes in detail the invention. It will be apparent to those skilled in the art that modification of materials and methods may be practiced without departing from the purpose and intent of this disclosure.

EXAMPLE

The human GM-CSF expression plasmid, pAKG-151 used in this example consists of about 3800 base pairs and includes the following sequences (see FIG. 1):

(a) The double tandem promoter 1pp/1ac linked to the ompA signal sequence; Ghrayeb, et al., EMBO J., Vol. 3 (10), 2437–2442 (1984).

(b) The coding sequence for mature Hu-GM-CSF; Lee, et al., Proc. Natl. Acad. Sci. USA, Vol. 82, 4360–4364 (July 1985). The 5' end of this coding sequence is fused with the 3' end of the ompA signal coding sequence.

(c) The lac I gene for the expression of the lac repressor; Farabaugh, Nature, Vol. 274, 765–769 (Aug. 24, 1978).

(d) The temperature sensitive replicon, rep copl Ts, derived from the plasmid pVU 208; Hakkart, et al., Mol. Gen. Genet.; Vol. 183, 326–332 (1981).

(e) The kan$^r$ gene for the expression of aminoglycoside 3' phosphotransferase II; Beck, et al., Gene 19, 327–336 (1982).

Cultivate a culture of *E. coli* strain 294 harboring the plasmid pAKG-151 in 200 ml of broth contained in a 2 liter baffled shake flask at 30° C. The broth consists of 30 g/l of casein hydrolysate, 20 g/l of yeast extract, 20 g/l of glycerol, 10 mg/l of kanamycin, 5 g/l $KH_2PO_4$, 1 g/l $MgSO_4.7H_2O$, 0.1 ml/l of an antifoam agent and water. The initial pH is adjusted to 7.0 with sodium hydroxide. Agitate until the cellular density of the culture reaches about 4 optical density units (lightpath 1 cm, 660 μm). Add 0.4 mM of isopropyl-β-D-thiogalactoside and continue the fermentation for about 3 hours attaining cellular density of about 9 optical density units. Then add 85% phosphoric acid to obtain a pH 4.0 followed by 50% trichloroacetic acid until pH 2.0 is attained. Agitate the acidified suspension for 1 hour at 30° C., centrifuge the suspension, discard the supernatant and resuspend the bacterial pellet in 0.1M sodium phosphate buffer pH 8.5. The pH of the resulting suspension is adjusted to pH 7.0–7.5 with 1N sodium hydroxide. Adjust the final biomass concentration of the neutral suspension to correspond to about 30 optical density units of untreated culture. Agitate the neutral suspension for 30 minutes at 4° C., centrifuge and discard the pellet. The supernatant contains extracted recombinant human granulocyte macrophage colony stimulating factor (GM-CSF).

We claim:

1. A method of extracting granulocyte macrophage-colony stimulating factor (GM-CSF) from GM-CSF-expressing bacterial cells comprising:
   (a) treating a suspension of GM-CSF containing bacterial cells with an acid and an enhancing agent;
   (b) removing substantially all of the suspension liquid from the cells;
   (c) preparing a second suspension of the treated cells;
   (d) neutralizing said second suspension; and
   (e) separating the GM-CSF containing liquid from the suspended cells.

2. The method according to claim 1, wherein said suspension in step (a) is acidified to a pH of about 1.5 to 3.0.

3. The method according to claim 1, wherein said suspension in step (a) is treated with phosphoric acid, hydrochloric acid, nitric acid or sulfuric acid.

4. The method according to claim 1, wherein said suspension is treated with phosphoric acid.

5. The method according to claim 1, wherein the enhancing agent is a chaotropic ion selected from the group consisting of trichloroacetate, perchlorate, thiocyanate and guanidine.

6. The method according to claim 5, wherein the enhancing agent is the chaotropic ion trichloroacetate.

7. The method according to claim 1 wherein the enhancing agent is a non-chaotropic salt selected from the group consisting of sodium chloride and sodium phosphate.

8. The method according to claim 1 wherein the enhancing agent is urea.

9. The method according to claim 1, wherein the suspension in step (a) is acidified to pH of about 2.0 to 2.2.

10. The method according to claim 1, wherein step (a) is carried out at a temperature from about 10° C. to 40° C.

11. The method according to claim 10, wherein step (a) is carried out at a temperature of 25° C.

12. The method according to claim 1, wherein said second suspension is neutralized with sodium hydroxide.

13. The method according to claim 1, wherein the second suspension is neutralized to a pH of about 6 to 9.

14. The method according to claim 1, wherein the second suspension is neutralized to pH of about 7.2 to 7.6.

15. The method according to claim 1, wherein steps (b) thru (e) are carried out at a temperature of from about 0° to 40° C.

16. The method according to claim 1, wherein steps (b) thru (e) are carried out at a temperature of from about 0° to 4° C.

17. The method according to claim 1, wherein the bacterium is selected from the group consisting of *Escherichia coli, Bacillus subtilis* and *Streptomyces coelicolor.*

18. The method according to claim 1 wherein the bacterium is *Escherichia coli.*

* * * * *